United States Patent [19]

Dethlefsen

[11] Patent Number: 4,871,545

[45] Date of Patent: Oct. 3, 1989

[54] PHARMACEUTICAL COMBINATION OF NIFEDIPINE AND SALBUTAMOL

[75] Inventor: Uwe Dethlefsen, Aachen, Fed. Rep. of Germany

[73] Assignee: Euro-Celtique S.A., Luxembourg

[21] Appl. No.: 108,910

[22] Filed: Oct. 15, 1987

[30] Foreign Application Priority Data

Oct. 18, 1986 [DE] Fed. Rep. of Germany ....... 3635522

[51] Int. Cl.$^4$ ............................................... A61K 9/26
[52] U.S. Cl. .................................... 424/470; 424/468; 424/475; 424/489; 424/499; 424/501
[58] Field of Search ............... 424/468, 474, 470, 475, 424/482, 489, 499, 501, 476

[56] References Cited

U.S. PATENT DOCUMENTS

| | | | |
|---|---|---|---|
| 4,317,930 | 3/1982 | Hirose et al. | 260/501.18 |
| 4,337,272 | 6/1982 | Bernareggi et al. | 514/597 |
| 4,582,840 | 4/1986 | Garthoff et al. | 514/356 |
| 4,652,563 | 3/1987 | Slater | 514/247 |
| 4,716,041 | 12/1987 | Kjornaes et al. | 424/468 |
| 4,719,226 | 1/1988 | Otsuka et al. | 514/447 |
| 4,758,433 | 7/1988 | Johnson et al. | 514/468 |

Primary Examiner—Thurman K. Page
Attorney, Agent, or Firm—Merchant, Gould, Smith, Edell, Welter & Schmidt

[57] ABSTRACT

Nifedipine is a well-known calcium antagonist, and salbutamol is a much used bronchodilator. Yet a pharmaceutical combination containing both substances is not known. Prior experience with the administration of nifedipine in combination with beta$_2$-sympathomimetica did not make any combinatory effect appear probable. It was further to be feared that any combinatory effect would be accompanied by correspondingly increased side effects. The new pharmaceutical composition is nevertheless intended to provide a combination of nifedipine with a beta$_2$-sympathomimeticum usable for systemic application especially in cases of asthmatic diseases. According to the invention, the pharmaceutical combination contains salbutamol besides nifedipine. The combined effect of the active substances is super-additive and synergistic. Nevertheless, no addition of side effects is experienced. The therapeutic effect of the combination corresponds approximately to the maximum achievable improvement.

18 Claims, 9 Drawing Sheets

PHARMACEUTICAL COMBINATION OF NIFEDIPINE AND SALBUTAMOL

DESCRIPTION

The invention concerns a pharmaceutical combination which contains nifedipine.

Nifedipine (dimethyl-1,4-dihydro-2,6-dimethyl-4-(2-nitrophenyl)-3,5-pyridine-dicarboxylate) is a known calcium antagonist and is employed predominantly in the treatment of coronary heart disease and hypertension. In addition, nifedipine exhibits a not very marked bronchodilating effect.

Salbutamol (1-(4-hydroxy-3-hydroxymethylphenyl)-2-t-butylaminoethanol) is a known beta$_2$-sympathomimetic; by stimulating the $\beta$-receptors, it has a relaxant effect on the bronchial muscles. Salbutamol is therefore a widely used bronchodilator.

Lever, Corris and Gibson have undertaken studies to establish whether there are benefits from employing nifedipine together with salbutamol in the treatment of asthma (Thorax, 39, 1984, 576–578). In this study, asthma patients were each given a dose of 20 mg of nifedipine, followed 30 minutes later by the inhalation of 200 micrograms of salbutamol. Nifedipine was therefore administered orally, and salbutamol specifically by inhalation. Although the authors of this study are of the opinion that they were able to demonstrate that the bronchodilating effect of the salbutamol was prolonged by the administration of nifedipine, it was later justifiably disputed (Thorax, 40, 1985, 399) that a conclusion of this sort could be drawn from the measurements published by Lever et al.

In a more recent study undertaken by Rolla, Arossa, Bucca and Bugiani (Int. J. Clin. Pharm. Res. VI (5), 409–413 (1986)) the effects of 20 mg orally administered nifedipine and 400 mcg inhaled salbutamol were investigated in a double-blind cross over design. In contrast to the findings of Lever, Corris and Gibson, there was no statistically significant effect of nifedipin pretreatment as compared with the effects produced by salbutamol alone.

Similar results were obtained by Molho, Gruzman, Katz, Lidgi and Chaniac (CHEST 91, 5 (1978). According to this study, oral administration of 10 mg or 20 mg nifedipine, followed by inhalation of 2,5 mg salbutamol, did not reveal any influence of nifedipine on the bronchodilatory effect produced by salbutamol.

Taking into account the well-known variability of lung function data in asthma patient, the results of the above-mentioned studies actually are not in significant contradiction with each other. It is only the interpretation of the results, which differs in every specific case.

In all above-mentioned studies, the nifedipine pre-treatment was carried out by oral administration of a fast-release encapsulated formulation. Subsequent salbutamol administration was by inhalation. With such a sequence and way of administration, the measured pharmacodynamic effects of salbutamol administration following nifedipine pretreatment are so small, if at all observable, that the effects are largely determined by the actual experimental set-up.

Accordingly, these studies show no significant effect to be gained from combining orally administered nifedipine with subsequently inhaled salbutamol which could make the use of such a combination desirable for clinical applications.

It has now surprisingly been found by the inventors, that a statistically highly significant super-additive synergistic effect is obtained, when nifedipine and salbutamol are simultaneously administered in the form of a pharmaceutical combination. This combination is especially advantageous, if the weight ratio of nifedipine to salbutamol in the combination lies between 5:1 and 1:1, especially at or near 5:2. The combination is preferably administered orally, as a solid dosage form, especially a tablet containing the solid active substances. As a dosage unit, this tablet advantageously contains 5 mg nifedipine and 2,4 mg salbutamol sulphate, corresponding to 2 mg salbutamol. The total content of nifedipine in this dosage unit is lower than that necessary to develop significant cardiovascular effects of nifedipine, the total content of salbutamol being at the same time at a level appropriate to achieve the bronchodilating effect of salbutamol alone, but basically below the level at which side effects would appear.

The oral administration of nifedipine together with salbutamol has not previously been undertaken. It is yet extremely advantageous to formulate nifedipine together with salbutamol as a single pharmaceutical combination for systemic application, especially in asthmatic diseases.

However, against this is the fear that the side-effects of the active substances might overlap with an additive effect, which would be extremely significant as far as its therapeutic value is concerned, in view of the known side-effects of salbutamol (tremor, giddiness, changes in pulse rate and blood pressure) and the possible tachycardiac effects of nifedipine.

Such undesirable tachycardiac effects were e.g. observed in the study of K. Svedmyr, C. -G. Löfdahl and N. Svedmyr (Allergy 1984, 39, 17–22).

A further problem to be expected in the treatment of pulmonary troubles with nifedipine is loss of ciliary response due to calcium removal. A study by Sanderson and Dirksen (Proc. Natl. Acat. Sci. USA, 83, 7302–7306, 1986) shows that calcium antagonists like verapamil (and accordingly nifedipine) lead to a dramatic decrease in beat frequency of the cilia and therefore to reduced mucociliary clearance. This leads to enhanced accumulation of inhaled substances in the pulmonary tract. This effect severely limits the potential of nifedipine (and other calcium antagonists) in the treatment of patients with chronic obstructive respiratory diseases.

In addition a study of the combined systemic administration of nifedipine and a beta$_2$-sympathomimetic, namely terbutaline, does not encourage expectations that a combination of nifedipine with bronchodilators of this sort might be promising. According to the results of Tomioka et al. (Arerug, 31, (12), 1982, 1215–1221), a combination of nifedipine with terbutaline has no effect on respiratory function different from that of terbutaline alone. Evidently there would accordingly be no point in risking the side-effects of nifedipine if the effect of the bronchodilator was not increased by adding nifedipine to it.

Against this background, the inventors nevertheless set themselves the task of finding a combination of nifedipine with a beta$_2$-sympathomimetic which can be made available in the form of a pharmaceutical combination for systemic application, especially in asthmatic diseases.

The solution to this problem is that according to the invention the pharmaceutical combination containing nifedipine is characterized by the fact that the combination contains salbutamol in addition to nifedipine.

The ratio of nifedipine to salbutamol by weight in the combination according to the invention lies between 5:1 and 1:1, is preferentially between 5:1 and 5:3, and is most particularly preferred to be between 5:2 and 5:3. It was demonstrated in experiments that specifically a ratio by weight of five parts nifedipine to two parts salbutamol can be employed to particular advantage.

It is of advantage to formulate the pharmaceutical combination in a presentation in which the total content of nifedipine in any dosage unit is less than that necessary to develop significant cardiovascular effects of nifedipine, and that the total content of salbutamol in the dosage unit is at a level appropriate to achieve the bronchodilating effect of salbutamol alone but basically below the level at which side-effects would appear. In particular the unit dose, for example an orally administered tablet, contains 5 mg of nifedipine and 2 mg of salbutamol. This dosage unit thus has a content of nifedipine which is just below the limit at which significant cardiovascular effects of nifedipine occur. The content of salbutamol in the dosage unit is so low that, although a noticeable bronchodilating effect does occur, the side-effects typical of salbutamol are still largely suppressed.

Surprisingly, a formulation of this sort nevertheless has a marked effect as a pharmaceutical combination, which in most patients almost achieves the maximum possible therapeutic improvement. Although the quantities of nifedipine and salbutamol individually would not be sufficient for such an effect, it is achieved by the combination of these active substances. The effect obtained goes far beyond a simple, additive effect of the active substances, i.e. a super-additive, synergistic effect of the active substance combination is observed. This synergistic effect is both functional and sequential - a feature rarely observed with combinations. The active substance combination not only acts for a longer time overall than the respective half-lives of the components would lead one to expect, but the organic effect is also greater than the sum of the individual effects to be expected of these components.

In view of this synergistic, mutual potentiation of effect between nifedipine and salbutamol, it is particularly surprising that no corresponding increase in side-effects is observed. The overall pattern of side-effects is not super-additive and is not even additive. In fact the combination can be employed in most cases to the point where patients present almost no remaining obstruction of the airways and without any disturbing side-effects being observed at all. Thus the pattern of side-effects with the combination is on about the same level as the side-effects produced by the individual components in the same concentrations. In particular, it is surprising that no tachycardiac effects appear.

An additional, completely surprising effect observed in patients treated with the combination of nifedipine and salbutamol according to this invention is, that the ciliar beat frequency is not decreased, but instead even synergistically increased by the combination. Thus, in combination with salbutamol, nifedipine has a completely different effect on ciliated cells and therefore mucociliary clearance than nifedipine alone.

The invention thus constitutes a pharmaceutical preparation which enables a combination of nifedipine and a beta$_2$-sympathomimetic to be administered systemically, to achieve almost maximal efficacy and at the same time to remain essentially free of side-effects. The combination can be administered orally in the simplest way in the form of a tablet, and thus avoids the cost and difficulties which result from the oral administration of nifedipine separately from the application of the beta$_2$-sympathomimetic by inhalation.

In addition to nifedipine and salbutamol, or even instead of these substances, the pharmaceutical combination may contain suitable derivatives of salbutamol and/or of nifedipine which produce comparable effects. In that event the proportions by weight would be chosen such that they also correspond to concentrations of the individual components which are below the threshold of side-effects, but so that the combination together develops the desired therapeutic effect on the basis of synergy. Especially, the salbutamol can be present in the form of a salbutamol salt, like salbutamol sulphate, with the salt content equivalent to the desired content of free salbutamol base as specified above.

Nifedipine (or a suitable nifedipine derivative) is preferably present in the pharmaceutical combination in a controlled-release formulation, so that the retard effect frequently sought after with nifedipine preparations is achieved. In contrast, the salbutamol is preferably present in the pharmaceutical combination in a formulation which promotes its release, so that it will develop its effect as soon as possible after administration.

Without any intention of limiting the scope of this invention to any specific scientific explanation, the striking differences between the effects produced by the prior art treatments and the invention are probably due to the following facts:

It appears that the sequence of administration of nifedipine and salbutamol is decisive for obtaining the desired pharmacodynamic effect. In prior art, the combination of nifedipine and salbutamol is administered stepwise with a delay of 30 minutes or more. Both nifedipine and salbutamol are administered in fast-release formulations.

In contrast thereto, the combination according to the invention provides simultaneous administration of nifedipine and salbutamol. The salbutamol is released very quickly, leading to fast bronchodilation, which can be explained on the basis of the well-known action of beta-sympathomimetica. The release of nifedipine only starts together with that of salbutamol. This appears to lead to a pharmacodynamic retardation of the effect produced by the nifedipine, which was not observed before and is as yet not very well understood. Nifedipine content in plasma increases slowly and remains for a very long time. Based on present molecular biological knowledge of the action of calcium channel blockers like nifedipine, it is assumed that the effect of salbutamol is amplified and prolonged by stabilization of the intra- and extra-cellular calcium metabolism.

This effect is especially pronounced, when the pharmaceutical combination according to the invention contains nifedipine in a slow release (retard) formulation, and at the same time contains salbutamol in a fast release formulation.

It is evident that the described effects cannot possibly be observed when administering salbutamol to patients pretreated with nifedipine, when the salbutamol is administered 30 minutes or longer after the nifedipine. When using the prior art methods, the pharmacodynamic retardation and consequently the functional and sequential synergism provided by the invention's combination is not achievable.

We will now amplify the surprising synergistic effect of the pharmaceutical combination according to this invention, on the basis of comparative studies.

These studies comprised an initial series of experiments in which the effect of salbutamol alone was compared with the effect of a combination of salbutamol and nifedipine in vitro. Tracheal muscles from bovines and guinea pigs were used as the experimental material.

A second series of experiments was undertaken in a clinical trial in asthma patients, in which nifedipine alone, salbutamol alone, or the combination according to the invention was employed.

"BRIEF DESCRIPTION OF THE DRAWINGS"

The results of the first series of experiments are shown in FIGS. 1 to 3, and the results of the second series in FIGS. 4 to 9.

In detail, these show the following.

In the first series of experiments, dose-response curves were recorded for salbutamol in the absence and in the presence of nifedipine in potassium-tonicised strips of tracheal muscle (3–4 in each instance) from bovines and from guinea-pigs. The effects of salbutamol in the absence or presence of a certain concentration of nifedipine were compared with the calculated effects of an additive combination. The method for producing an additive dose-response curve of this sort is described in J. Pharmacol. Meth. 4, (1980), 179–188; Errat. 5, (1981), 183.

This curve is the dose-response curve which would be obtained if salbutamol were to be tested in the presence of a specific, predetermined concentration of salbutamol itself or of a substitute substance for salbutamol. A similar method was employed to determine the scatter of the additive curve, but instead of the mean value for the effect of nifedipine and instead of the curve of mean values for salbutamol, the corresponding points of the variation in SEM (standard error) were used. This makes it possible to perform a statistical comparison between the observed effect of the combination salbutamol-nifedipine on the one hand, and the corresponding additive combination in the middle and upper range of concentrations of salbutamol on the other (Meth. Find. Exptl. Clin. Pharmacol. 4, (1982), 371-377). In addition to the total effects of salbutamol and nifedipine, the net effects of salbutamol in the presence of nifedipine were evaluated and these were compared with the effects of salbutamol in the absence of nifedipine (shown in the smaller diagrams inserted in FIGS. 1-3 respectively).

Figure 1:
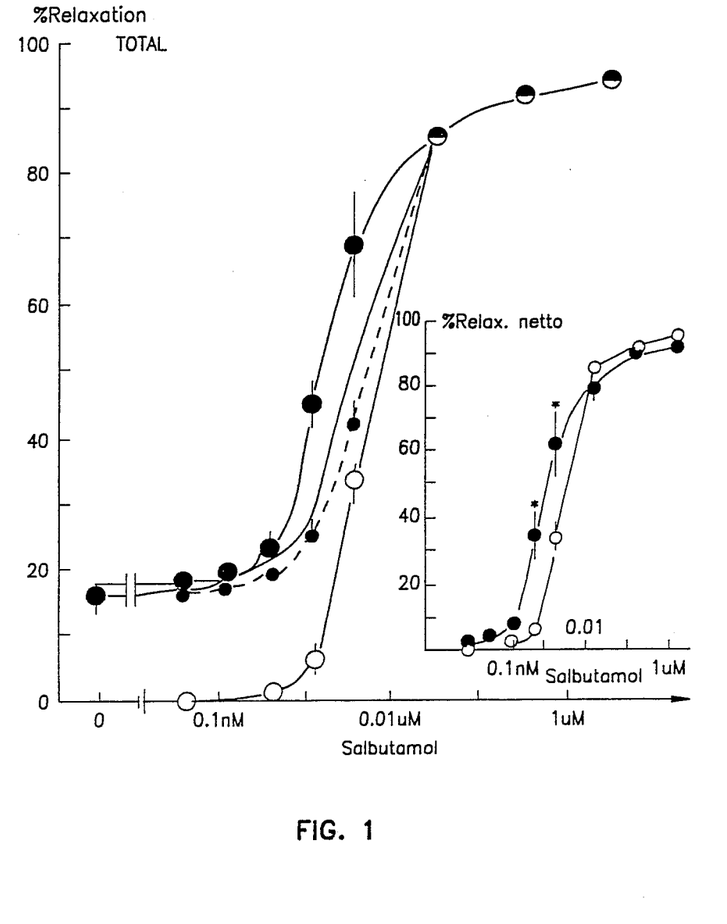
FIG. 1: Dose-response curves for salbutamol with and without the addition of 3 nM nifedipine, measured in bovine tracheal muscles.

The dose-response curve shown in FIG. 1 for the relaxant effect of salbutamol on potassium-tonicised preparations of bovine tracheal muscle shows firstly the effect of salbutamol alone (white dots), and in the presence of 3 nM nifedipine (solid black dots). This shows the values obtained from experiments in four preparations of muscle. For the purposes of comparison, the curves are shown together with the expected effects of an additive combination which is indicated by a broken line. The continuous line drawn immediately above the broken line represents the maximum statistical deviation.

Figure 2:
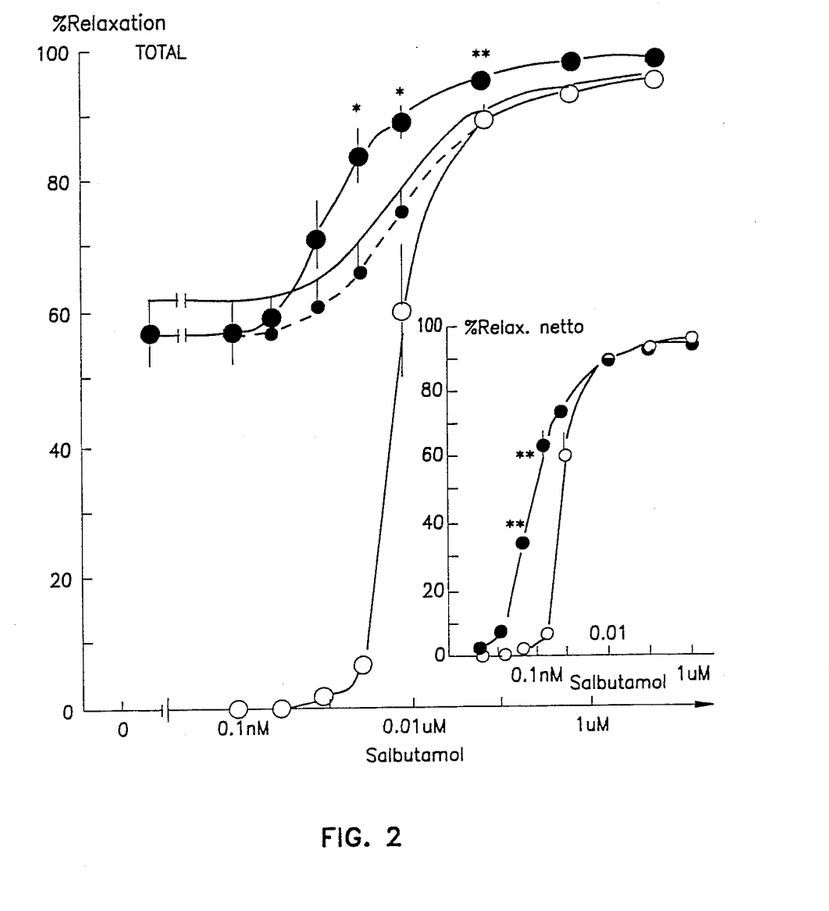
FIG. 2: A dose-response curve similar to FIG. 1, but for 10 nM nifedipine.
Figure 3:
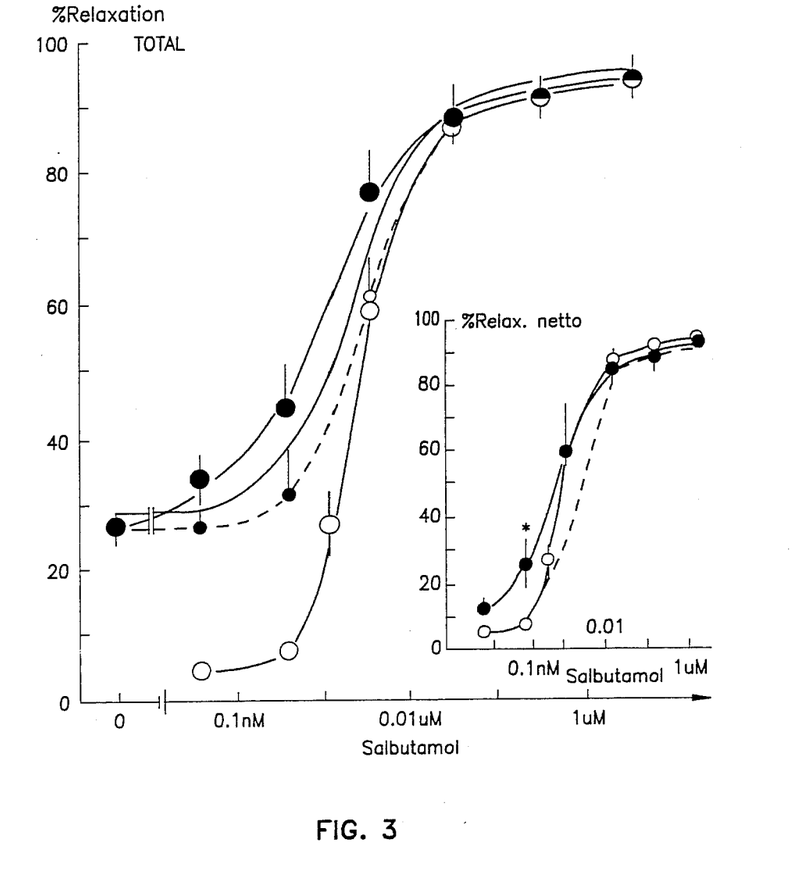
FIG. 3: Dose-response curves similar to FIG. 1, but measured in the tracheal muscles of guinea pigs.

As in FIGS. 2 and 3, this figure also has the total effects, which are statistically significantly greater than the effect of the corresponding additive combination, marked with one asterisk, and total effects which highly significantly exceed the additive effect are marked with two asterisks.

FIG. 1 shows that for the combination of salbutamol+3 nM nifedipine the total effect with about 5 nM salbutamol becomes super-additive, while the measured values are on the limit of significance. In this study, apart from the small number of strips of muscle, the slight intrinsic effect of 3 nM nifedipine was also decisive in causing the results to only just reach a level of statistical significance, and this makes it more difficult to distinguish clearly between super-additive total effects and purely additive effects. The net effect of salbutamol in the presence of nifedipine is significantly greater in the middle region of the curve than the effect of salbutamol in the absence of nifedipine, and this points to relatively marked intensification effects which go beyond independent, functionally synergistic effects. These findings provide indirect evidence of a super-additive effect, because the action of salbutamol in the absence of nifedipine is greater than the corresponding additive effect anyway. This is obvious in the statistically significant data of the smaller-scale curve inserted in FIG. 1, which shows the net effects of salbutamol in the presence of nifedipine (solid black dots) in comparison with the effect of salbutamol in the absence of nifedipine (white dots).

The experiments represented in FIG. 2 were conducted with four potassium-tonicised strips of bovine tracheal muscle, with a nifedipine concentration of 10 nM. The action of salbutamol in combination with nifedipine is unambiguously super-additive. All the values obtained with the combination exhibit total effects which with the middle to upper concentrations of salbutamol are significantly to highly significantly greater than the effect of the corresponding additive combination. Once again, the smaller-scale figure inserted in FIG. 2 shows intensified net effects of salbutamol in the presence of 10 nM nifedipine which were highly significant in the middle concentration range of the dose-response curve and argue in favour of a sequential type of potentiation.

The experiments represented in FIG. 3 were conducted with three potassium-tonicised strips of tracheal muscle from guinea-pigs. The smaller-scale curve inserted in the Figure gives the net effect of the additive combination, shown as a broken line.

FIG. 3 shows similar results in terms of the trend, as were already observed in bovine tracheal muscle. However, the total effect which appears to be super-additive with the salbutamol/nifedipine combination, cannot (yet) be significantly differentiated from additive effects. It is interesting that the net effect of salbutamol in the presence of nifedipine in one point was significantly greater than an independent, functionally synergistic effect. The latter is equivalent to an additive effect in this concentration range, so that the conclusion can be drawn that the same or a very similar intensification of the effect of the combination salbutamol/nifedipine, which was already demonstrated in bovine tracheal muscle is apparent in guinea pig tracheal muscle as well.

In summary, it was evident even in this first series of experiments that the relaxant effects of the combination salbutamol/nifedipine on tracheal muscle are super-additive and synergistically greater than those of the individual components, that this potentiation exceeds a functional synergy and indicates a sequential synergy.

The preliminary experiments in the second series aimed to investigate the synergy of the combination salbutamol/nifedipine in asthma patients. In a controlled, triple cross-over study, the efficacy and tolerance of the individual substances were tested in comparison with the combination, with lung function being monitored using body plethysmography.

The study was conducted in twelve hospitalised patients with chronic obstructive respiratory tract diseases (ten patients with asthma and two with chronic obstructive bronchitis). The mean age of the patients was 39 years and ranged between 24 and 54 years old. Their mean height was 172 cm, and their average weight was 68 kg (ranging from 54 to 84 kg).

Patients were only accepted into the study if their initial airway resistance was within the range 6 to 12 cm $H_2O/l/sec$, and if their forced expiratory volume in one second $FEV_1$ after inhalation of two shots each of 200 micrograms of fenoterol exhibited an increase of at least 15%.

Only suitable patients who needed no additional therapy were included in the study. The concomitant medication with controlled-dosage aerosols was reduced to a minimum and recorded in a special trial protocol. Steps were taken to ensure that the controlled-dosage aerosols were not used for at least eight hours before the examination of lung function.

Patients with accompanying diseases which might prejudice the assessment of the treatment on account of their severely progressive nature, were not accepted into this study.

The patients were treated either with nifedipine in dosage units of 5 mg, salbutamol in dosage units of 2 mg or with the new combination of nifedipine+salbutamol in the ratio of 5 mg: 2 mg per dosage unit. Doses administered on each occasion at 08.00 and at 20.00 were either 2×5 mg nifedipine or 2×2 mg salbutamol or 2× the combination with 5 mg nifedipine and 2 mg salbutamol. The sequence of administration was randomised, with a wash-out phase of two days after each form of treatment.

Steps were taken to ensure that no patient had received methyl xanthines 24 hours before the examination (lung function test and determination of reversibility), nor any beta-sympathomimetics for 8 hours previously—even in the form of a controlled-dosage aerosol.

Lung function (Raw, TGV, VC, $FEV_1$ and PEF) and the patients' pulse and blood pressure were measured on the first and third day always at the same times in the day—08.00, 10.00 and 15.00. On the third day of the trial, after the last measurement of lung function, reversibility was again determined 15 minutes after inhalation of 400 micrograms of fenoterol.

The determination of initial airway resistance and the measurement of reversibility at the start of the study (R) show that the patients had a moderate degree of obstruction with a mean value of 7.3 cm $H_2O/l/sec$., which decreased to 3.1 cm $H_2O/l/sec$. after inhalation of 400 micrograms of fenoterol, corresponding to a reduction of 57% (in relation to the intial value). This preliminary determination of reversibility is indicated in FIGS. 4 to 7 with an R.

Figure 4:
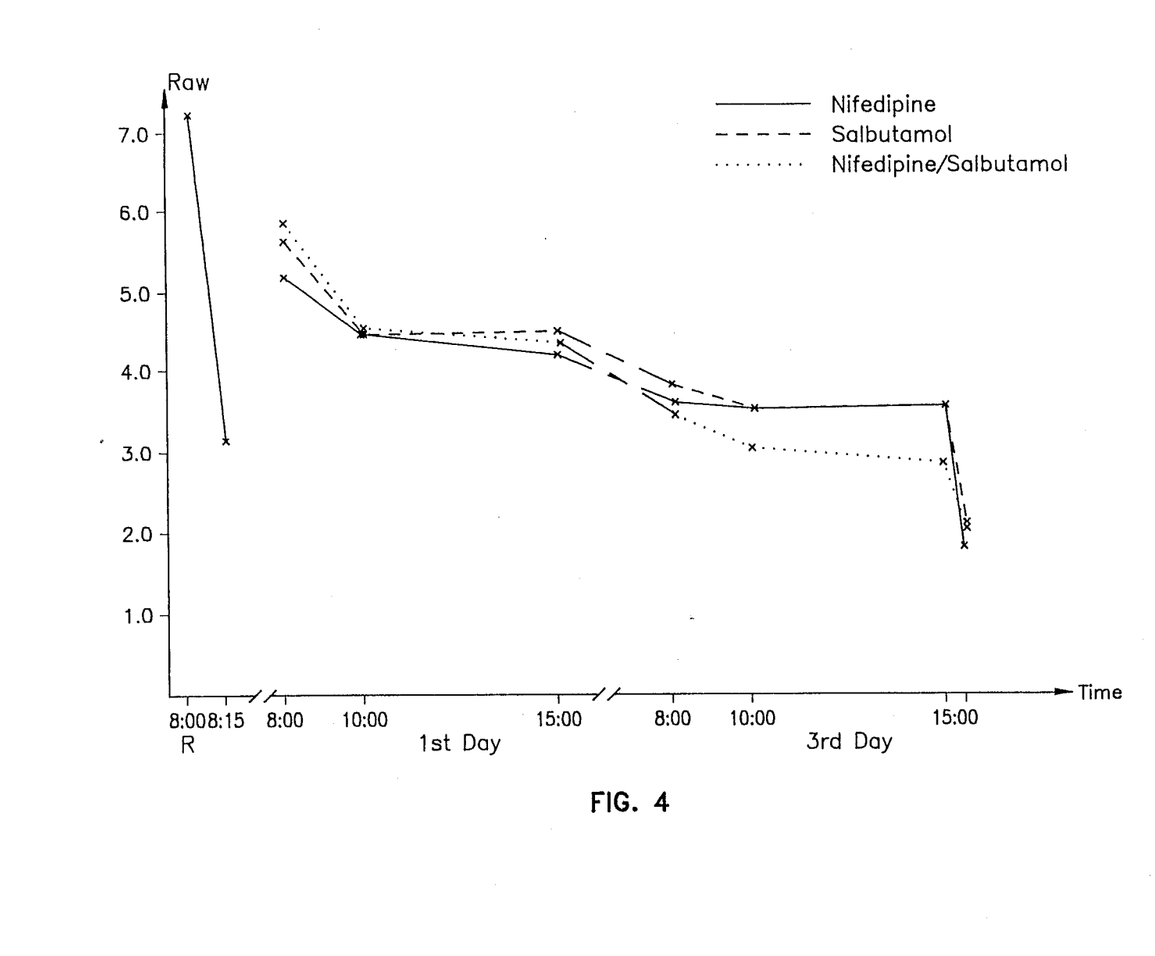
FIG. 4: The changes in airway resistance in asthma patients under treatment with nifedipine alone or salbutamol alone, or with a combination of nifedipine+- salbutamol.
Figure 5:
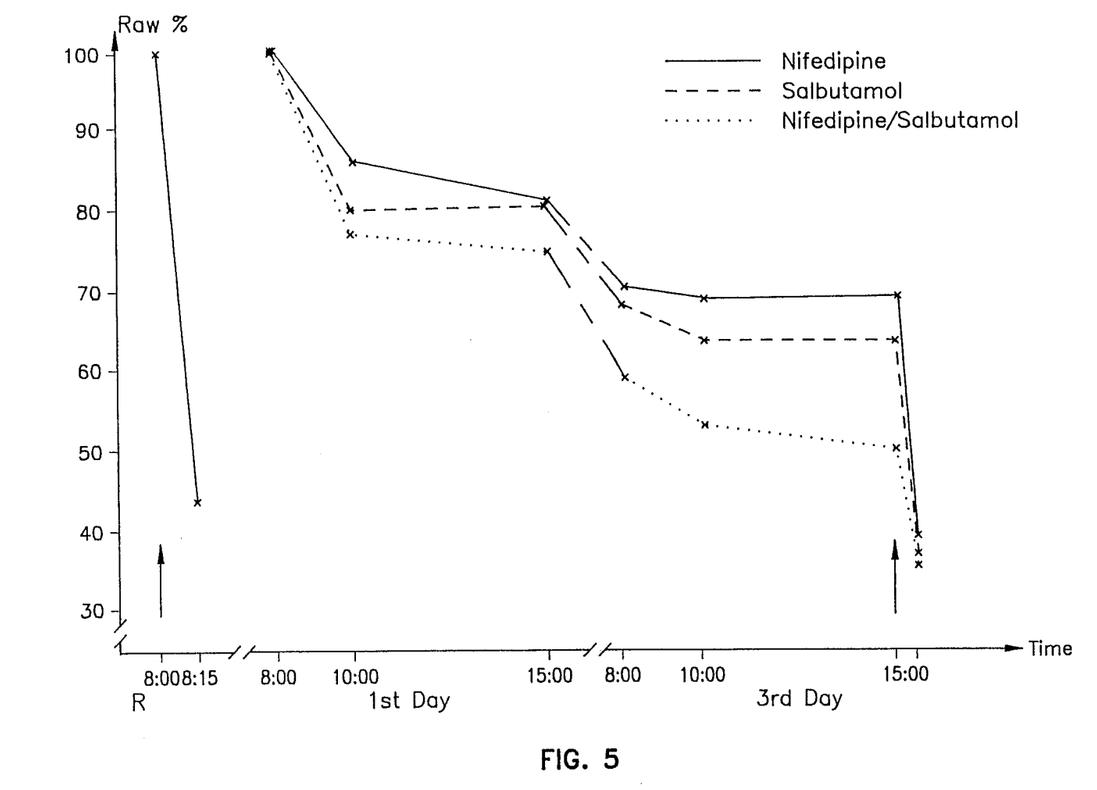
FIG. 5: The change in airway resistance as in FIG. 4, expressed as percentages.

The change in airway resistance Raw shown in FIGS. 4 and 5 (mean airway resistance of the 12 patients) indicates very clearly that the effect of the combination is statistically highly significantly superior to the effects of the individual substances. In particular it is evident that at the end of the treatment period the results achieved were substantially closer to the maximum degree of improvement achievable by therapy when the combination was administered. This is illustrated by the residual reversibility, measured at 15.00 on the third day after again inhaling 400 micrograms of fenoterol (black arrow).

Figure 6:
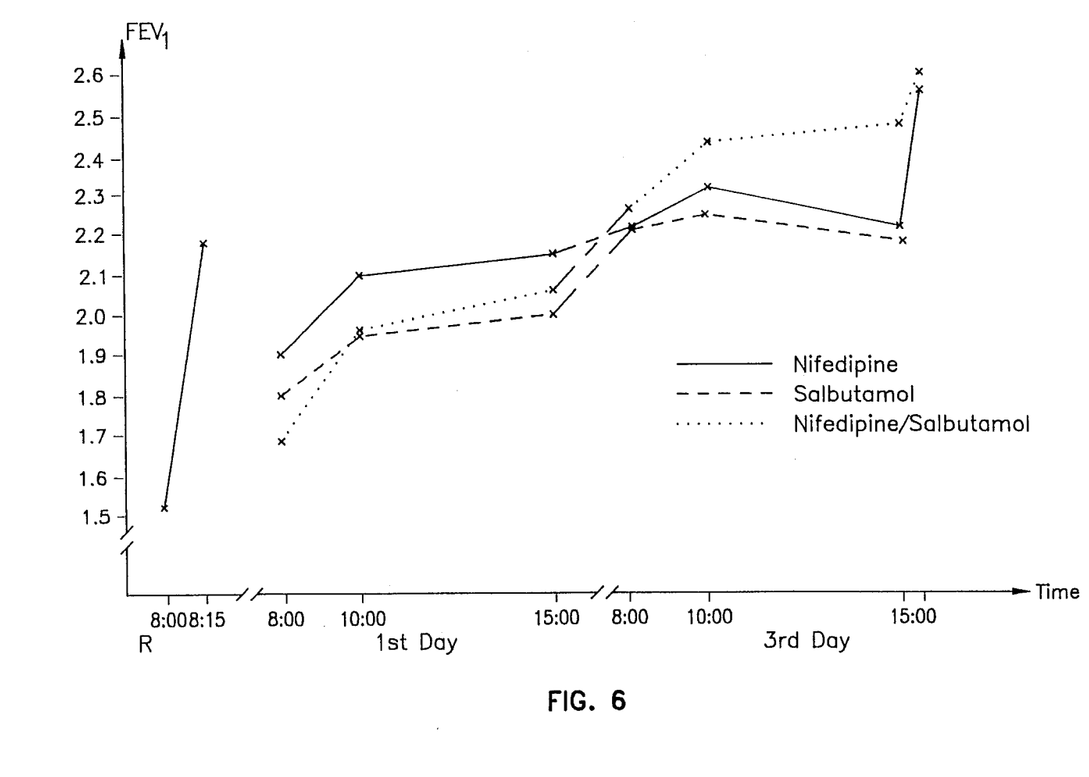
FIG. 6: The change in forced expiratory volume in one second ($FEV_1$), measured in asthma patients under treatment with nifedipine alone, salbutamol alone, or with the combination nifedipine+salbutamol.
Figure 7:
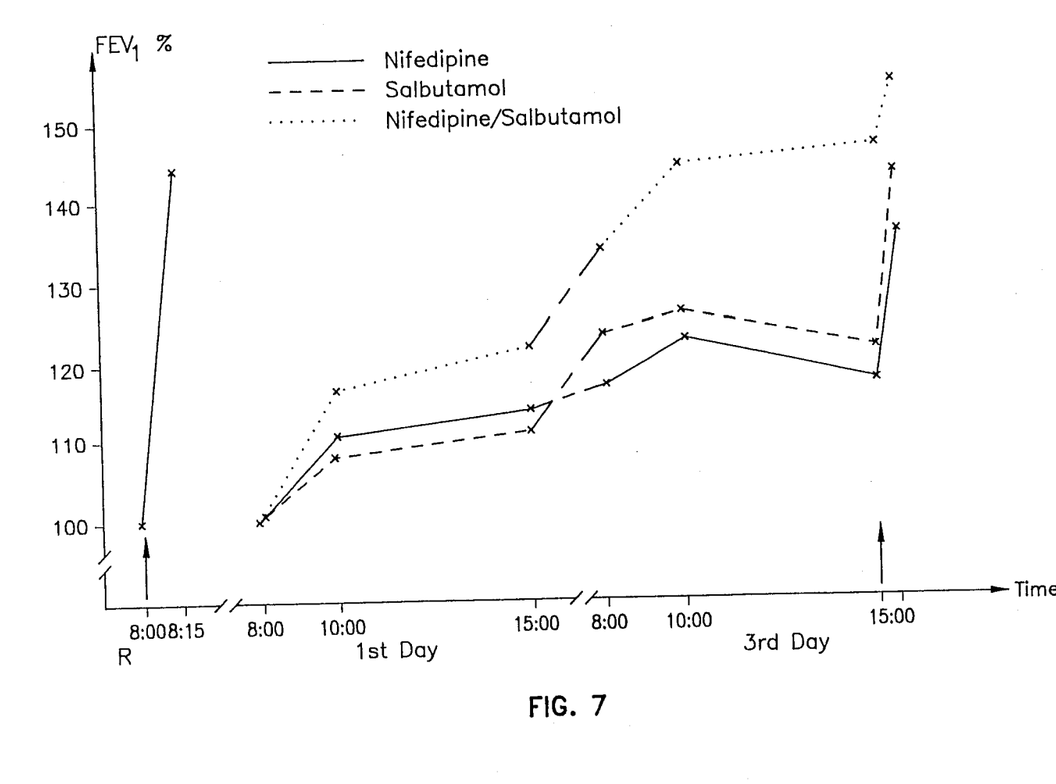
FIG. 7: The change in forced expiratory volume ($FEV_1$) similar to FIG. 6, expressed as percentages.

FIGS. 6 and 7 show the change in forced expiratory volume in one second $FEV_1$, once again on the basis of the mean value for 12 patients. Again, reversibility was determined before the start of the actual series of experiments by measurements before and after inhalation of 400 micrograms of fenoterol (R, black arrow), and after the conclusion of the experiments residual reversibility was measured in the same way (black arrow, at 15.00 on the third day).

At the start of the trial the patients exhibited a mean $FEV_1$ of 1.5 liters, which increased by 45% to 2.2 liters after inhalation of 400 micrograms of fenoterol (reversibility). On the third day of teratment a significant increase in forced expiratory volume was only identified in the patients treated with the new combination of active substances. Lung function was highly significantly better on the third day in patients treated with the new combination, than in patients treated with the individual substances. The determination of residual reversibility on the third day showed that a markedly greater improvement was achievable by inhalation of the controlled-dosage aerosol in patients both on nifedipine alone and on salbutamol alone, whereas with the new combination specified by the inventor, the residual reversibility corresponded on average to an increase in $FEV_1$ of only 130 ml. In particular, FIG. 7 makes it clear that hardly any further improvement was possible in the condition achieved with the new combination. These patients exhibited practically no remaining obstruction of the airways.

Figure 8:
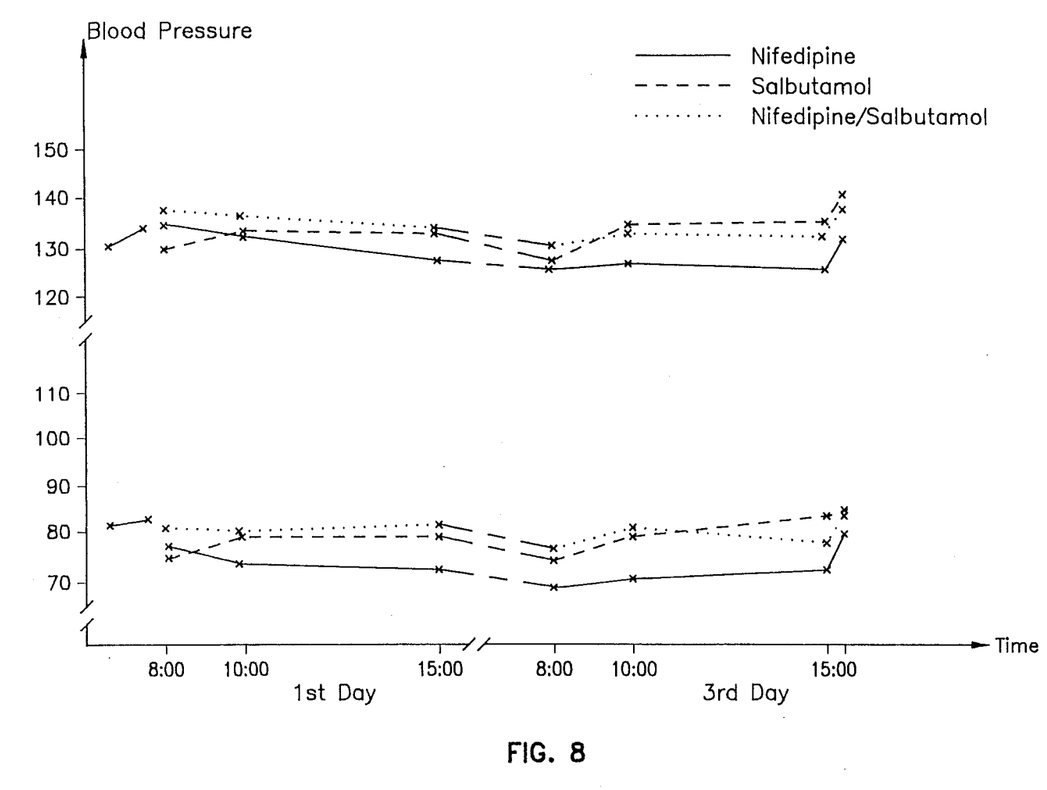
FIG. 8: The change in mean blood pressures in patients during treatment, as in FIGS. 4 to 7.
Figure 9:
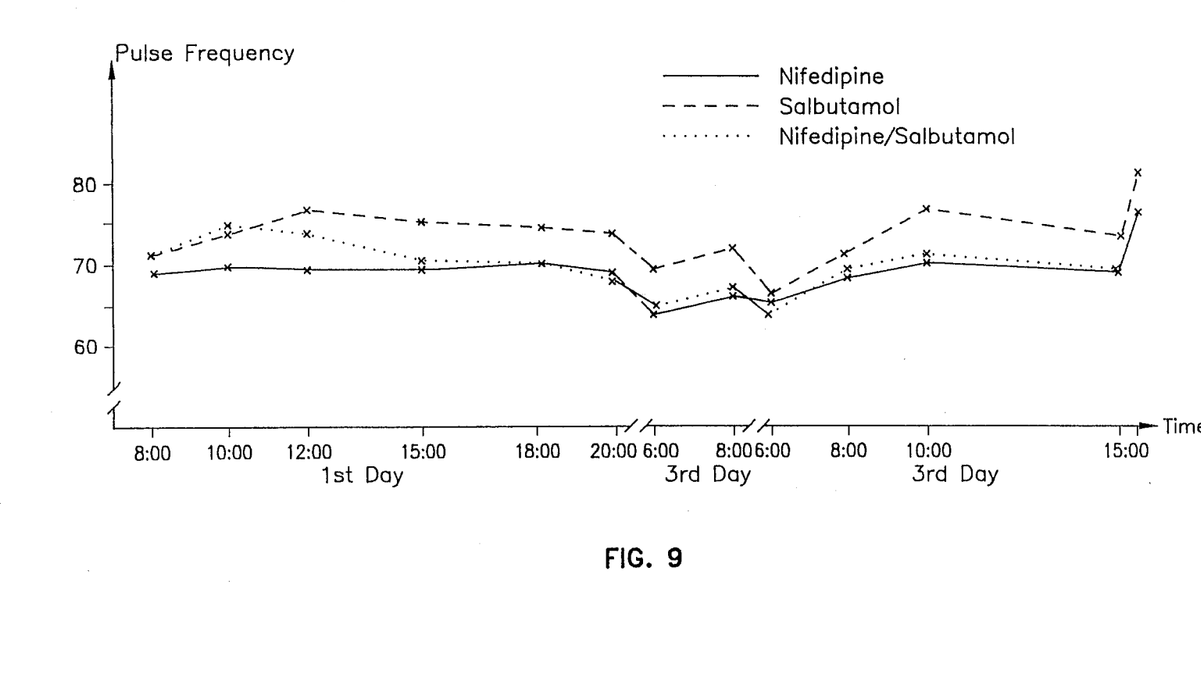
FIG. 9: The change in mean pulse rates in patients during treatment as in FIGS. 4 to 7.

To monitor side-effects in particular, the patients' mean blood pressures were measured (FIG. 8) and their mean pulse rates were determined (FIG. 9) over the entire period of the trial. As the Figures clearly show, the side-effects under treatment with the new combination according to the invention are not appreciably greater and in some cases are even less than those under treatment with corresponding doses of the individual active substances.

In evaluating these results, it can be stated that the known effects of salbutamol were also evident in these experiments under treatment with this substance alone. With regard to nifedipine in a twice daily dose of 10 mg a bronchodilating effect was also established, which turned out to be very different between individuals: The two forms of treatment with the individual substances are therefore completely in agreement with the action claimed for them in the literature. This shows that the design of the trial and the evaluation of the data were relevant to clinical practice.

The distinct superiority of the combination compared with the individual substances is shown by the comparison of lung function measurements. The clinically significant improvement in lung function achieved with the combination was confirmed to be statistically highly significant. Neither pulse nor blood pressure during the study showed any differences of clinical relevance. No side-effects were observed.

Thus the combination of active substances according to the invention has also proved to be highly effective synergistically in vivo in the clinical trial. The newly invented combination of active substances therefore makes it possible to provide a pharmaceutical preparation which permits systemic treatment with the combination of nifedipine+salbutamol to be conducted in the simplest way, which achieves a marked reduction in the clinical symptoms and which makes it possible to achieve a high degree of bronchodilation without appreciable side-effects occuring.

The following examples show solid unit dosage forms of the combination in form of tablets, which showed the same advantageous effects as given above with reference to the second series of preliminary experiments (clinical tests):

EXAMPLE 1

200 g nifedipine with a specific surface of 0.5 m$^2$/g and 96 g salbutamol sulphate were mixed with 1600 g microcrystalline cellulose, 2200 g lactose and 300 g corn starch. A further 240 g corn starch were mixed with water and 60 g polyvinylpyrrolidone (Kollidon K25) to form a paste. The nifedipine/salbutamol sulphate dry mix was granulated by thoroughly mixing it with this paste, and the granules were subsequently dried. After drying the granules, 40 g magnesium stearate and 200 g polyethylen glycol (average molecular weight 6000) were added. The dry mixture was pressed into tablets of 124 mg tablet weight and a tablet diameter of 8 mm.

Since the nifedipine is light-sensitive, the tablets were coated with a suspension of 43,75 g dry Opadry OY-S-4939, 1 g polyethylen glycol (average molecular weight 4000–6000) and 1250 g water. This amount of suspension is sufficient for coating approximately 1500 g of tablets and provides them with a dark red protective coating.

In this formulation, nifedipine bioavailability is controlled by the specific surface. The fairly small specific surface, corresponding to an average particle size of about 20 μm, leads to controlled slow release of the nifedipine.

EXAMPLE 2

200 g nifedipine and 96 g salbutamol sulphate were mixed with 5155.7 g lactose-monohydrate, 176.6 g polyvinylpyrrolidone (Kollidon K30), 187.7 g polyvinylpyrrolidone (Kollidon CL), 40 g magnesium stearate and 160 g talcum. The dry mixture was pressed into tablets of tablet weight 150 mg and tablet diameter 8 mm.

The resulting tablets were coated with an Opadry-suspension, as above in Example 1.

The tablets according to Example 2 give especially fast tablet dissolution and therefore especially fast release of the salbutamol. Slower, retarded nifedipine release can again be provided by suitable choice of nifedipine specific surface.

While the tablets of both examples have contents of nifedipine and salbutamol sulphate corresponding practically exactly to 5 mg nifedipine and 2,4 mg salbutamol sulphate (equivalent to 2 mg salbutamol), the amounts of nifedipine and salbutamol sulphate in each tablet could be different, with the desired synergistic effect being still achieved without side-effects.

I claim:

1. A pharmaceutical preparation comprising nifedipine or a pharmaceutically acceptable salt thereof and salbutamol or a pharmaceutically acceptable salt thereof wherein the weight ratio of nifedipine or its salt to salbutamol or its salt is from about 5:1 to 1:1.

2. A preparation according to claim 1, comprising nifedipine and salbutamol or a pharmaceutically acceptable salt thereof.

3. A preparation according to claim 1, wherein the preparation is in a solid form.

4. A preparation according to claim 1, wherein the weight ratio of nifedipine or its salt to salbutamol or its salt in the preparation is between 5 to 1 and 5 to 3.

5. A preparation according to claim 4 wherein the weight ratio of nifedipine or its salt to salbutamol or its salt in the preparation is between 5 to 2 and 5 to 3.

6. A preparation according to claim 5 wherein the weight ratio of nifedipine or its salt to salbutamol or its salt in the preparation is 5 to 2.

7. A preparation according to claim 6, in unit dosage form, containing 5 mg of nifedipine and 2 mg of salbutamol.

8. A preparation according to claim 6, in unit dosage form, containing 5 mg of nifedipine and 2.4 mg of salbutamol sulphate.

9. A preparation according to claim 1, in unit dosage form, wherein the total content of nifedipine or its salt is lower than that necessary to develop significant cardiovascular effects, and the total content of salbutamol or its salt is sufficient to achieve a bronchodilating effect but insufficient to develop side effects.

10. A preparation according to claim 1 in a unit dosage form suitable for oral administration.

11. A preparation according to claim 10 in the form of a tablet.

12. A preparation according to claim 1, wherein the nifedipine or the pharmaceutically acceptable salt thereof is incorporated into a controlled release formulation.

13. A prepartion according to claim 1, comprising nifedipine having a specific surface area of less than 1 m$^2$gm$^{-1}$ and a water-soluble salbutamol salt.

14. A preparation according to claim 13 comprising nifedipine having a specific surface area of about 0.5 m$^2$gm$^{-1}$.

15. A preparation according to claim 1, in unit dosage form, wherein the unit dosage form is coated with a pharmaceutically acceptable, light protective coating.

16. A preparation according to claim 15 wherein the coating comprises a coloured, laquer coating.

17. A method for the treatment of chronic obstructive airway disease comprising administering to a patient suffering from the disease, a therapeutically active dose of a pharmaceutical preparation comprising nifedipine or a pharmaceutically acceptable salt thereof and salbutamol or a pharmaceutically acceptable salt thereof wherein the weight ratio of nifedipine or its salt to salbutamol or its salt is from about 5:1 to about 1:1.

18. A method according to claim 17 wherein the preparation is in a solid form.

* * * * *